United States Patent [19]

Merwin

[11] Patent Number: 4,719,913
[45] Date of Patent: Jan. 19, 1988

[54] SURGICAL APPARATUS FOR CONTOURING IMPLANTS

[75] Inventor: Gerald E. Merwin, Gainesville, Fla.

[73] Assignee: University of Florida, Gainesville, Fla.

[21] Appl. No.: 3,507

[22] Filed: Jan. 15, 1987

Related U.S. Application Data

[62] Division of Ser. No. 737,535, May 24, 1985, Pat. No. 4,656,995.

[51] Int. Cl.⁴ .............................................. A61B 17/00
[52] U.S. Cl. ................................. 128/303 R; 409/211
[58] Field of Search ............. 128/303 R, 305; 408/76; 409/204, 206, 211

[56] References Cited

U.S. PATENT DOCUMENTS 2,480,737  8/1949  Jayle .................................... 128/305

FOREIGN PATENT DOCUMENTS 991160  5/1965  United Kingdom .................. 408/76

Primary Examiner—Stephen F. Husar
Attorney, Agent, or Firm—Kerkam, Stowell, Kondracki & Clarke

[57] ABSTRACT

Surgical apparatus for use in contouring medical implants comprises a transparent enclosure adapted to be located on a metallic work surface in an operating theater, the enclosure being sized to enable manipulation of an implant therein by a surgeon for contouring, a stand connected to the enclosure for adjustably positioning and fixing a surgical drill in a preselected orientation with respect to the work surface such that the drill bit projects throughout an opening into the interior of the enclosure, the stand carrying a magnetic mechanism so as to enable the stand to be immobilized with respect to the work surface, and a movable cutting block having a disposable cutting surface thereon. The stand is connected to the enclosure by a metal tongue, slidably carried by the stand, which is received within a slot on the underside of the enclosure, and the cutting block is formed with a magnetic mechanism so as to enable immobilization of the cutting block with respect to the tongue.

6 Claims, 3 Drawing Figures

SURGICAL APPARATUS FOR CONTOURING IMPLANTS

This is a division of application Ser. No. 737,535, filed May 24, 1985, now U.S. Pat. No. 4,656,995.

BACKGROUND OF THE INVENTION

This invention relates generally to surgical apparatus useful for contouring medical implants and the like, and more particularly to apparatus for preventing loss, damage or contamination of an implant during a contouring process.

Surgical specialities such as otolaryngology, plastic and reconstructed surgery, neurosurgery, and orthopedic surgery, frequently involve the implantation of autograft, homograft, or alloplastic or other non-natural materials in a patient. Such implants must be contoured very precisely during surgery to an exacting size and shape in accordance with the needs of a particular patient. Contouring of implants, which is analogous to a micro-machining operation, may generally involve measuring, cutting, drilling, chipping, ronguering, splintering with biting forceps or otherwise shaping the implant. Such operations require care to prevent damage, loss or contamination of the implant. In using a surgical drill, for example, to cut or shape an implant, the surgeon typically holds a small drill hand piece in one hand and the implant in the other hand, and manipulates the drill and the implant to accomplish the required contouring. Care must be exercised during this process to avoid over-shaping of the implant, which may render it unusable, and to ensure that the drill burr does not catch the implant and cause it to fly away. Similarly, in cutting or splintering an implant using biting forceps, care must be exercised to avoid loss of control of the implant by the surgeon.

Autograft materials are obtained at some risk in morbidity to the patient, and if the implant is lost or otherwise damaged or contaminated during the contouring procedure, harvesting of further material from the patient becomes necessary. Homograft implants represent a significant expense to obtain and store, and if lost, damaged or contaminated represent a significant financial loss, as well as a loss of valuable human material. Alloplastic and other artificial material implants also represent a significant financial loss if they are lost, damaged or contaminated during the contouring process.

It is desirable to provide apparatus which will assist a surgeon in the contouring of implants and which will minimize a possibility of loss, damage or contamination of the implants, and it is to this end that the present invention is directed.

SUMMARY OF THE INVENTION

The invention affords surgical apparatus which is particularly well adapted for use in a surgical theater or operating room in connection with the contouring of medical implants and the like for preventing loss, damage, or contamination of the implant during the contouring process.

In accordance with one aspect, the invention provides surgical apparatus which comprises an enclosure which is adapted to be disposed on an operating theater work surface, the enclosure being sized to receive and enable manipulation and contouring within its interior of a medical implant, and having first, second and third openings therein. The first opening is formed to enable insertion of the implant into the interior of the enclosure and through which the implant may be manipulated. The second opening is formed to enable contouring and irrigating tool means to be inserted into the interior of the enclosure for contouring the implant; and the third opening is a drain opening for draining irrigation liquid from the enclosure. The enclosure is formed of transparent material to enable illumination of the interior and to facilitate visual access thereto. The enclosure is preferably formed with a top surface having a portion which is inclined with respect to the first opening to facilitate visual access to the interior of the enclosure and with a second substantially horizontal portion located adjacent to the second opening. The first inclined portion may have formed on its interior surface a groove to promote heading of irrigation fluid in order to prevent the fluid from running down the inclined interior surface and obstructing visual access. The apparatus may further comprise stand means formed to enable the contouring and irrigating tool means to be adjustably positioned so that it may be inserted through the second opening into the interior of the enclosure; means for mobilizing the stand means with respect to the work surface; and means for connecting the enclosure and the stand means in alignment so as to permit insertion of the contouring and irrigating means through the second opening.

In another aspect, the invention affords surgical apparatus for use in contouring medical implants which comprises a stand for holding a surgical drill tool. The stand may comprise a base having means for releasably connecting the base to a work surface in a surgical theater; a support member extending upwardly from the base; a first bracket slidably disposed on the support member; means for fixing the first bracket in a preselected location on the support member; a second bracket pivotally connected to the first bracket such that the second bracket may pivot about an axis with respect to the first bracket, the second bracket having clamp means for supporting the surgical drill tool; and means for fixing the second bracket in a preselected orientation about the pivot with respect to the first bracket so as to hold the surgical drill tool in predetermined location with respect to the work surface.

In still another aspect, the invention affords surgical apparatus for use in contouring medical implants and the like which comprises a base, means carried by the base for releasably attaching the base to a work surface in a surgical theater so as to immobilize the base; and a removable cutting surface disposed on an upper surface of the base. The removable cutting surface may comprise a layer of flexible material having depending projections, and the upper surface of the base may be formed with corresponding apertures for receiving the projections to enable the cutting surface to be removably attached to the base.

DESCRIPTION OF THE PREFERRED EMBODIMENT

Figure 1:
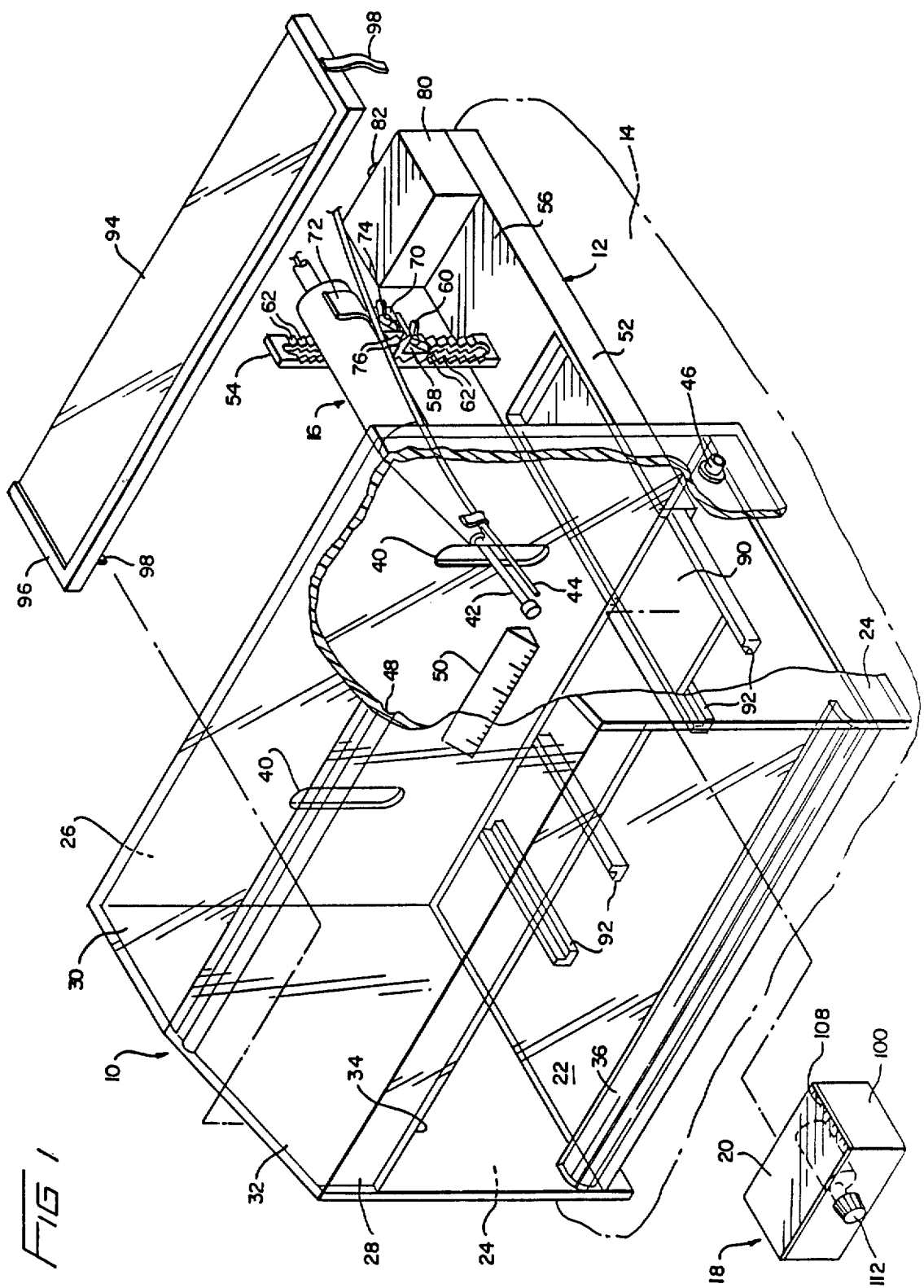
FIG. 1 is a perspective view, partially broken away, of surgical apparatus in accordance with the invention.

As indicated above, the invention provides surgical apparatus which is particularly well adapted for use in a surgical theater or operating room for aiding a surgeon in contouring medical implants and the like, and it will be described in that environment. As will become apparent, however, this is illustrative of only one utility of the invention.

With reference to the figures, and as will be described in more detail hereinafter, the principal components of surgical apparatus in accordance with the invention may include a box-like enclosure 10 within which a medical implant (not illustrated) or the like may be manipulated and contoured, a stand 12 formed to be immobilized with respect to a work surface 14 in a surgical theater or operating room, such as a stainless steel table, and to enable a surgical drill hand piece and irrigating tool 16 to be adjustably positioned and fixed in a desired orientation, and a cutting board or block 18 having a cutting surface 20 thereon, which block may be received within enclosure 10 and immobilized. Although enclosure 10, stand 12, and cutting block 18 cooperate in a highly advantageous manner to aid a surgeon in contouring a medical implant and in preventing loss, damage or contamination of the implant, each may also be used advantageously alone as will become apparent from the following description.

Figure 2:
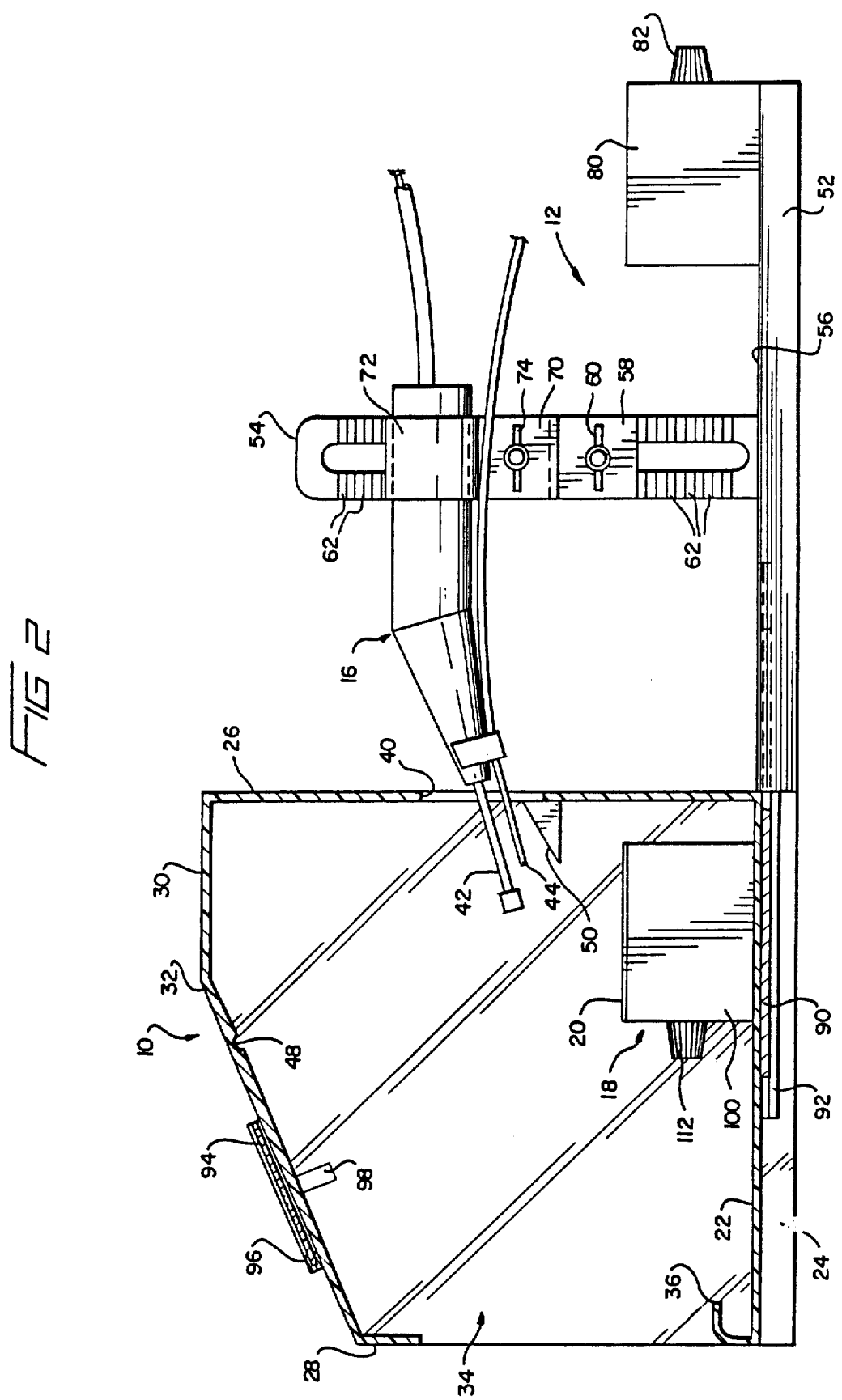
FIG. 2 is a side view, partially in cross-section, of the apparatus of FIG. 1.

In more detail, enclosure 10 comprises a bottom wall 22, side walls 24, a rear wall 26, a front wall 28, and a top wall having a rear substantially horizontal portion 30 and a front inclined portion 32. The enclosure is preferably formed of transparent material, such as clear plexiglass, for example, which can withstand ethylene oxide sterilization. Clear plexiglass is advantageous in that it is inexpensive and will afford an enclosure which may be reused for a number of surgical procedures before it is ultimately discarded. Enclosure 10 is intended to be located on table 14 with the surgeon standing or seated on a stool in front of the enclosure. Accordingly, front wall 28 of the enclosure is formed with an opening 34 to provide access to the interior of the enclosure and to enable manipulation of the implant therein. Visual access to the interior is principally through inclined top surface 32. The transparent walls conveniently enable the interior of the enclosure to be illuminated by the operating room lights or other special lighting devices. If desired, the bottom wall 22 and the bottom portion of the rear wall 26 (up to approximately its midpoint, for example) may be made opaque and have a dull dark color finish to afford good contrast with the implant. As shown in FIGS. 1 and 2, the bottom lip portion 36 of the front wall may be curved inwardly to form an arm or hand rest for the surgeon. Enclosure 10 may be any convenient size. For example, an enclosure 9½ inches high, 9 inches deep, and 18 inches wide has been found to be satisfactory to afford sufficient room for manipulation and contouring of most implants. As shown in FIG. 1, opening 34 preferably extends the full width of the enclosure.

Rear wall 26 may be formed with one or more openings 40, such as elongated slots as shown in FIG. 1, to enable the drill bit 42 and irrigation fluid outlet tube 44 of the drill hand piece 16 to be inserted into the interior of the enclosure. As will be described in more detail shortly, stand 12 is formed to enable the drill hand piece and, accordingly, the drill bit and irrigation tube, to be positioned and fixed at a desired location and orientation. Irrigation tube 44, as is well known, sprays an irrigating fluid, such as water, onto the end of the drill bit and the implant. Enclosure 10 may also include a suction port 46 which is adapted to be connected to a standard suction line available in the operating room for removing excess irrigation fluid from the enclosure. Suction port 46 is preferably fitted with a mesh screen or the like (not shown) to prevent a small implant from being lost through the suction port should the implant be dropped. As is also shown in FIGS. 1 and 2, a transversely extending groove 48 is preferably formed in the interior surface of the inclined portion 32 of the top wall adjacent to horizontal portion 30. Since horizontal portion 30 is adjacent to the drill bit and irrigation tube, any irrigating fluid sprayed onto the interior of the top wall will primarily be on horizontal portion 30. The horizontal portion enables the fluid to bead and fall to the bottom of the enclosure rather than running down the inclined portion 32 and obstructing the surgeon's vision. Groove 48 also serves to stop fluid from running down the inclined portion and promotes beading of the fluid. As is further shown in the figures, a graduated measuring scale 50 may be disposed on the interior of rear wall 26 to enable measurements to be made on the implant during the contouring process.

Drill stand 12 may comprise a base 52 having a slotted support member 54 extending upwardly from the upper surface 56 of the base. A generally S-shaped bracket 58 may be slidably disposed for vertical movement on support member 54, and may be fitted with a height adjustment mechanism 60, such as a bolt and wing nut, to enable the vertical position of the bracket to be fixed on the support member. The mating surfaces of the support member and bracket may be formed with corresponding ridges and grooves 62 to prevent the bracket from slipping. A second bracket 70 having a clamp mechanism 72, such as spring steel clips or the like, for supporting the drill hand piece may be connected to bracket 58 by another bolt and nut arrangement 74 so as to enable the second bracket to be pivoted about a substantially horizontal axis with respect to the first bracket and its position to be fixed. The mating surfaces of brackets 58 and 70 may have corresponding radial grooves and ridges 76 to prevent bracket 70 from slipping once it is fixed.

Brackets 58 and 70 allow the height and inclination of the drill hand piece to be adjusted so that the drill bit 42 may be positioned and fixed at a desired orientation. Support member 54 is preferably positioned on base 52 such that the longitudinal axis of the drill and the longitudinal centerline of the base substantially coincide. Drill stand 12 is preferably formed so that it may be immobilized with respect to table 14. This advantageously enables drill bit 42 to be held securely fixed at a desired position and orientation during use. The surgeon manipulates the implant with respect to the drill bit, which is rotating at a fixed position, in order to shape the implant. In contrast to present practice whereby the surgeon holds a drill hand piece in one hand and the implant in the other hand and manipulates both the hand piece and the implant for shaping, the risk of over-shaping and damage or possible loss of the implant is minimized by holding the position of the drill bit securely fixed and this arrangement affords better, more accurate control over contouring.

To accomplish immobilization of the drill stand, base 52 may have an enclosure 80 formed on its rear portion which encloses a strong magnet eccentrically mounted on a shaft which may be rotated by a knob 82. As will be described in more detail shortly in connection with cutting block 18 which may employ a similar arrangement. Turning the knob enables the magnet to be positioned adjacent to the metal table 14. The attraction between the magnet and the table prevents movement of the stand as pressure is exerted on the drill bit during contouring. Turning the knob 180°, so that the magnet points away from the table, enables the stand to be moved easily.

Drill stand 12 may, of course, be used advantageously with or without enclosure 10. When used with enclosure 10, however, it is desirable to connect the enclosure to the drill stand to prevent movement of the enclosure. For this purpose, base 52 of the drill stand may slidably carry a tongue 90, which is preferably of metal such as stainless steel. Tongue 90 is adapted to be slid longitudinally outward from the front end of the base and to be received in a slot formed by a pair of L-shaped channels 92 attached to the underside of bottom wall 22 of the enclosure, as shown. As shown in the figures, side walls 24 of the enclosure preferably extend below the bottom surface of bottom wall 22 by a distance such that when the enclosure is resting on table 14 the underside of the bottom wall will be at the same height as the tongue projecting from base 52. This enables both the enclosure and the drill stand to rest securely on the table when they are attached together. As shown in FIG. 1, L-shaped channels may be positioned on the underside of the bottom wall with respect to openings 40 in the rear wall such that when the drill stand and the enclosure are connected together drill bit 42 and irrigation tube 44 are aligned with and project through a corresponding opening 40 into the interior of the enclosure.

During surgery, the surgeon will harvest an implant from the patient (in the case of an autograft), or will obtain a sterile homograft or alloplastic implant, and will determine the specific needs and contour of the implant. The drill hand piece will be fitted with a selected drill bit and clamped in clamp 72 of the drill stand. The height and inclination of the hand piece will then be adjusted to a convenient orientation and fixed. The enclosure and drill stand will then be connected together such that the drill bit and irrigation tube extend into the interior of the enclosure. The surgeon will then place the implant within the enclosure and manipulate the implant relative to the fixed drill bit for contouring. Measurements may be made on the implant during contouring using scale 50 within the enclosure. The enclosure provides a sterile environment in which the implant may be contoured, and in the event the surgeon losses control of the implant, as by the drill bit catching the implant and causing it to fly from the surgeon's hands, the enclosure prevents the implant from flying away. If no drilling or final shaping of the implant with a drill is required, the enclosure may be used without the drill and drill stand. In this case, the implant is simply moved into the sterile enclosure by the surgeon, where it may be worked on using biting forceps, a knife, or other shaping instruments, without fear of loss of the implant and with good illumination and magnification, if needed, using a microscope or a magnifying lens 94 fitted into a frame 96 having clips 98, as of spring steel, which enable the lens to be clipped onto the inclined surface 32 of the enclosure as shown in the figures.

Figure 3:
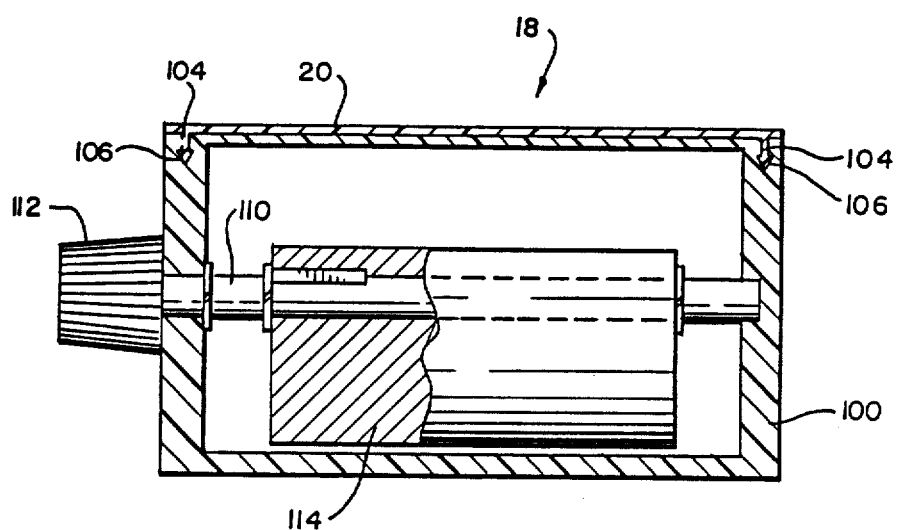
FIG. 3 is a cross-sectional view of a portion of the apparatus of FIG. 1.

For cutting of the implant using a knife or the like, it is desirable to have a good cutting surface upon which the implant may be rested. For this purpose, cutting board 18 may be used within the enclosure. Preferably, the cutting board comprises a hollow base 100 of hard material, such as acrylic, having a removable cutting surface 20. Preferably, cutting surface 20 is formed of a flexible material, such as vinyl, and is provided with depending projections 104 which are received in corresponding apertures 106 of base 100, as shown in FIG. 3. Projections 104 snap into apertures 106 to hold the cutting surface securely on the base. This construction advantageously allows the cutting surface to be discarded and replaced as needed. As shown in FIG. 1, the cutting surface may be provided with a graduated measuring scale 108 to enable measurements on the implant during contouring.

As previously noted, cutting block 18 may include a magnetic arrangement similar to that employed in stand 12 for immobilizing the cutting block within the enclosure. For this purpose, base 100 may be fitted with a rotatable shaft 110 controlled by a knob 112 with a strong magnet 114 eccentrically mounted on the shaft. Upon the cutting block being positioned within the enclosure over tongue 90 of the drill stand, and the knob 112 being turned to position the magnet downwardly, the attraction between the magnet and the tongue will hold the cutting block in place. Cutting block 18 may also be used outside of the enclosure, the rotating magnet arrangement advantageously enabling the cutting block to be immobilized on the surface of metal table 14.

As will be appreciated from the foregoing, surgical apparatus in accordance with the invention is highly advantageous in preventing loss, damage or contamination of an implant during contouring. Significantly, enclosure 10 may be constructed of inexpensive materials and discarded after several uses. Similarly, the replacable cutting surface of the cutting block is relatively inexpensive so that it may be discarded and replaced as needed without the necessity of replacing the entire cutting block. Furthermore, the drill stand, which enables the drill to be held in a fixed position reduces the probability of machining error by permitting greater control of the contouring process. While the enclosure, the drill stand, and the cutting block afford highly advantageous surgical apparatus when used together, the elements may also be used separately to advantage.

While a preferred embodiment of the invention has been shown and described, it will be appreciated by those skilled in the art that changes may be made in the foregoing embodiment without departing from the spirit and principles of the invention, the scope of which is defined in the appended claims.

What is claimed is:

1. Surgical apparatus for use in contouring medical implants and the like comprising a stand for holding a surgical drill tool, the stand comprising a base having means for releasably connecting the base to a work surface in a surgical theater; a fixed support member extending upwardly from the base; a first bracket slidably disposed on the fixed support member; first means for fixing the first bracket in a preselected location on the fixed support member; a second bracket pivotally connected to the first bracket, the second bracket carrying clamp means for supporting the surgical drill tool; second means for fixing the second bracket in a preselected orientation with respect to the first bracket so as to hold the surgical drill tool in a predetermined location with respect to the work surface; and means carried by the stand for immobilizing the stand with respect to the work surface.

2. The apparatus of claim 1, wherein said work surface is formed of metal, and said immobilizing means comprses magnetic means disposed within the base, and means for moving the magnetic means between a first position at which the magnetic means is adjacent to the work surface and a second position at which the magnetic means is positioned away from the work surface.

3. The apparatus of claim 2, wherein said magnetic means comprises a magnet, and said moving means comprises a shaft upon which the magnet is eccentrically mounted, the shaft being connected to a knob to enable rotation of the magnet between the first position and the second position.

4. The apparatus of claim 1, wherein the support member is slotted and has ridges and grooves formed to mate with corresponding ridges and grooves on the first bracket, and wherein the first fixing means comprises means for pressing the first bracket against the support member with said ridges and grooves in engagement.

5. The apparatus of claim 4, wherein the second bracket is pivotally connected to the first bracket for rotation about a substantially horizontal axis, and wherein the second fixing means comprises other corresponding ridges and grooves formed on other mating surfaces of the first and second brackets, and means for pressing the first and second brackets together with the other corresponding ridges and grooves in engagement.

6. The apparatus of claim 1, wherein said base slidably carries a projecting tonque to enable connection of the base to a transparent enclosure having an opening therein into which the surgical drill projects.

* * * * *

UNITED STATES PATENT AND TRADEMARK OFFICE
CERTIFICATE OF CORRECTION

PATENT NO. : 4,719,913

DATED : January 19, 1988

INVENTOR(S) : Gerald E. Merwin

It is certified that error appears in the above-identified patent and that said Letters Patent is hereby corrected as shown below:

Claim 6, column 7, line 5, "comprses" should read --comprises--;

Claim 6, column 8, line 14, "tonque" should read --tongue--.

Signed and Sealed this

Fourteenth Day of June, 1988

Attest:

DONALD J. QUIGG

Attesting Officer      Commissioner of Patents and Trademarks